(12) United States Patent
Gharda

(10) Patent No.: US 10,815,180 B2
(45) Date of Patent: Oct. 27, 2020

(54) PROCESS FOR PREPARATION OF 3,6-DICHLORO-2-METHOXYBENZOIC ACID (DICAMBA)

(71) Applicant: Keki Hormusji Gharda, Mumbai (IN)

(72) Inventor: Keki Hormusji Gharda, Mumbai (IN)

( * ) Notice: Subject to any disclaimer, the term of this patent is extended or adjusted under 35 U.S.C. 154(b) by 0 days.

(21) Appl. No.: 16/098,855

(22) PCT Filed: May 2, 2017

(86) PCT No.: PCT/IB2017/052536
§ 371 (c)(1),
(2) Date: Nov. 4, 2018

(87) PCT Pub. No.: WO2017/191554
PCT Pub. Date: Nov. 9, 2017

(65) Prior Publication Data
US 2019/0119189 A1    Apr. 25, 2019

(30) Foreign Application Priority Data

May 4, 2016 (IN) .............................. 201621015588

(51) Int. Cl.
*A01N 37/10* (2006.01)
*C07C 51/09* (2006.01)
*C07C 51/15* (2006.01)
*C07C 59/64* (2006.01)
*C07C 67/31* (2006.01)
*C07C 37/045* (2006.01)

(52) U.S. Cl.
CPC .............. *C07C 51/09* (2013.01); *A01N 37/10* (2013.01); *C07C 37/045* (2013.01); *C07C 51/15* (2013.01); *C07C 59/64* (2013.01); *C07C 67/31* (2013.01)

(58) Field of Classification Search
None
See application file for complete search history.

(56) References Cited

FOREIGN PATENT DOCUMENTS

WO     2015/095284     6/2015

OTHER PUBLICATIONS

International Search Report issued in co-pending International Application No. PCT/IB2017/052536 dated Aug. 11, 2017.

*Primary Examiner* — Alton N Pryor
(74) *Attorney, Agent, or Firm* — Whiteford, Taylor & Preston, LLP; Peter J. Davis

(57) ABSTRACT

In the process of the present disclosure 3,6-dichloro-2-methoxybenzoic acid (DICAMBA) is prepared from 2,5-dichloroaniline in high purity and high yield. DICAMBA is obtained with purity greater than 98.5%.

20 Claims, No Drawings

PROCESS FOR PREPARATION OF 3,6-DICHLORO-2-METHOXYBENZOIC ACID (DICAMBA)

FIELD

The present disclosure relates to 3,6-Dichloro-2-methoxybenzoic acid (DICAMBA).

BACKGROUND 3,6-Dichloro-2-methoxybenzoic acid (DICAMBA) is an important and selective systemic herbicide. It is effective against annual and perennial broad-leaved weeds and brushed species in cereals, maize, sorghum, sugarcane, turf, pastures, range land and non-crop areas. DICAMBA is absorbed through roots as well as leaves and translocates throughout the plant. It mimics auxin, a plant growth regulator and at adequate concentrations, is known to increase plant growth rate that outgrows its nutrient supplies leading to death of the plant. DICAMBA in combination with phenoxy or other herbicides is used in pastures, range land, and non-crop areas to control weeds.

The processes for the preparation of DICAMBA are complex and DICAMBA produced therefrom has low purity, and low yield.

There is, therefore, felt a need for preparing 3,6-dichloro-2-methoxybenzoic acid (DICAMBA) with relatively high purity and developing a simple process with high yield.

OBJECTS

Some of the objects of the present disclosure, which at least one embodiment herein satisfies, are as follows.

It is an object of the present disclosure to ameliorate one or more problems of the prior art or to at least provide a useful alternative.

An object of the present disclosure is to provide a simple and easy process for the preparation of 3,6-dichloro-2-methoxybenzoic acid (DICAMBA).

Another object of the present disclosure is to provide 3,6-dichloro-2-methoxybenzoic acid (DICAMBA) with high purity.

Other objects and advantages of the present disclosure will be more apparent from the following description, which is not intended to limit the scope of the present disclosure.

SUMMARY

A process for the preparation of 3,6-dichloro-2-methoxybenzoic acid (DICAMBA) in accordance with the present disclosure involves diazotizing 2,5-dichloroaniline with nitrosylsulfuric acid in at least one first fluid medium at a temperature in the range of −15° C. to 50° C. to obtain 2,5-dichlorophenyldiazonium salt; hydroxylating the 2,5-dichlorophenyldiazonium salt by contacting the 2,5-dichlorophenyldiazonium salt with sulfuric acid at a temperature in the range of 150° C. to 170° C. to obtain 2,5-dichlorophenol and a residue comprising sulfuric acid, wherein the concentration of the sulfuric acid used for hydroxylating is in the range of 60% to 75% w/w, and wherein the residue comprising sulfuric acid is subjected to recovery of sulfuric acid; forming an alkali metal 2,5-dichlorophenolate by reacting 2,5-dichlorophenol with an alkali metal hydroxide in at least one second fluid medium, wherein the moisture content of the alkali metal 2,5-dichlorophenolate is in the range of 0.005 to 0.05% w/w; carboxylating the alkali metal 2,5-dichlorophenolate at a temperature in the range of 60° C. to 160° C. to obtain an alkali metal salt of 3,6-dichlorosalicylic acid; methylating the alkali metal salt of 3,6-dichloro salicylic acid, in at least one third fluid medium, with a methylating agent selected from the group consisting of methyl chloride ($CH_3Cl$) and dimethyl sulfate ($(CH_3)_2SO_4$) at a temperature in the range of 60° C. to 160° C. to obtain methyl 3,6-dichloro-2-methoxybenzoate (DICAMBA ester); and hydrolysing the DICAMBA ester at a temperature in the range of 50° C. to 130° C. to obtain DICAMBA. The DICAMBA obtained by the process of the present disclosure has purity in the range of 98 to 99.5%.

DETAILED DESCRIPTION 3,6-Dichloro-2-methoxybenzoic acid (DICAMBA) is an important herbicide. The present disclosure envisages a simple process for preparing DICAMBA with high purity.

The present disclosure provides a process for the preparation of DICAMBA (I) using a 2,5-dichloroaniline (II) as a starting material.

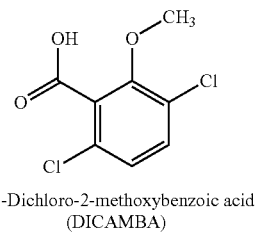

3,6-Dichloro-2-methoxybenzoic acid
(DICAMBA)

I

The process involves the following steps.

Step-1: Diazotization of 2,5-dichloroaniline (II) with Nitrosylsulfuric Acid Initially, 2,5-dichloroaniline (II) is diazotized with nitrosylsulfuric acid in at least one first fluid medium at a temperature in the range of −15 to 50° C. to obtain 2,5-dichlorophenyldiazonium salt (III).

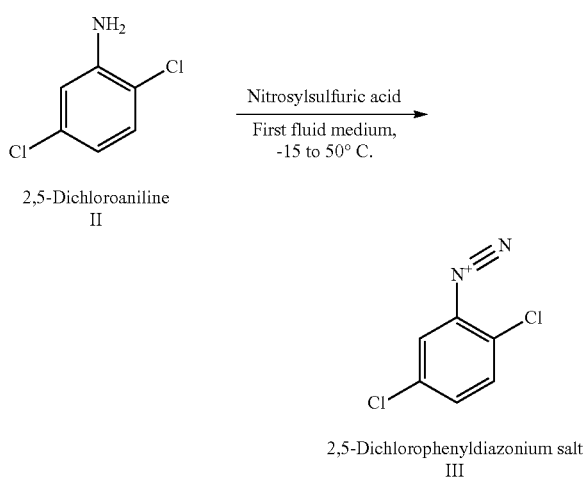

Step-2: Hydroxylation of 2,5-dichlorophenyldiazonium salt (III) with Sulfuric Acid ($H_2SO_4$)

The 2,5-dichlorophenyldiazonium salt (III) is hydroxylated by contacting with sulfuric acid at a temperature in the range of 150° C. to 170° C. to obtain 2,5-dichlorophenol (IV) and a residue comprising sulfuric acid. Concentration of the sulfuric acid used for hydroxylating is in the range of 60% to 75% w/w. Sulfuric acid is recovered from the residue comprising sulfuric acid.

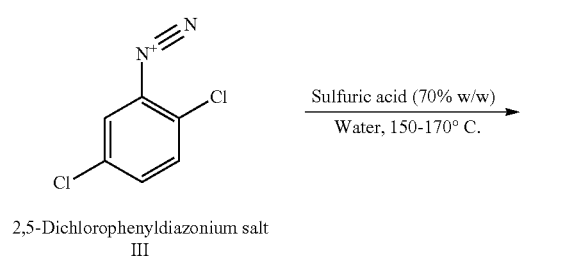

2,5-Dichlorophenyldiazonium salt
III 2,5-Dichlorophenol
IV

Step-3: Forming Alkali Metal 2,5-dichlorophenolate

An alkali metal 2,5-dichlorophenolate (V) is formed by reacting 2,5-dichlorophenol (IV) obtained in step-2, with an alkali metal hydroxide in at least one second fluid medium. Moisture content of the alkali metal 2,5-dichlorophenolate (V) so obtained is in the range of 0.005 to 0.05% w/w.

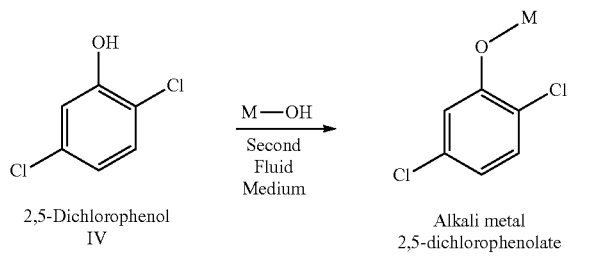

2,5-Dichlorophenol
IV

Alkali metal
2,5-dichlorophenolate
V

Step-4: Carboxylation of the Alkali Metal 2,5-dichlorophenolate with Carbon Dioxide ($CO_2$)

The alkali metal 2,5-dichlorophenolate (V) obtained in step-3, is carboxylated with carbon dioxide ($CO_2$) at a temperature in the range of 60 to 160° C., to obtain alkali metal salt of 3,6-dichlorosalicylic acid (VI).

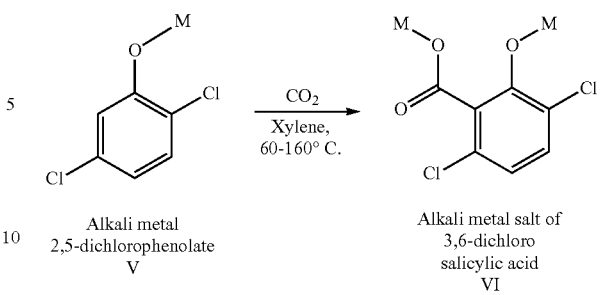

Alkali metal
2,5-dichlorophenolate
V

Alkali metal salt of
3,6-dichloro
salicylic acid
VI

Step-5: Methylation of the Alkali Metal Salt of 3,6-dichlorosalicylic Acid with a Methylating Agent The alkali metal salt of 3,6-dichlorosalicylic acid (VI) obtained in step-4, in at least one third fluid medium, is methylated with a methylating agent selected from the group consisting of methyl chloride ($CH_3Cl$), and dimethyl sulfate (($CH_3)_2SO_4$) at a temperature in the range of 60 to 160° C. to obtain methyl 3,6-dichloro-2-methoxybenzoate (DICAMBA ester, VII).

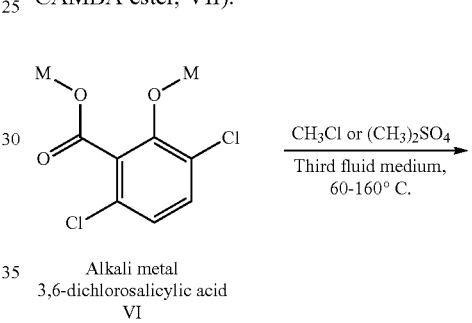

Alkali metal
3,6-dichlorosalicylic acid
VI

Methyl
3,6-dichloro-2-methoxybenzoate
VII

Step-6: Hydrolysing the DICAMBA Ester

The DICAMBA ester (VII) obtained in step-5, is hydrolysed at a temperature in the range of 50 to 130° C. to obtain DICAMBA (I).

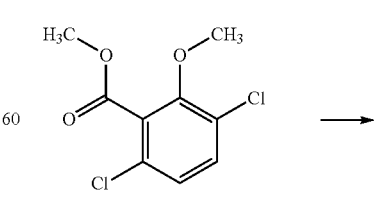

Methyl
3,6-dichloro-2-methoxybenzoate
VII

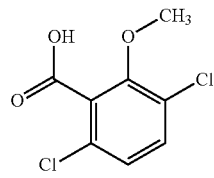

3,6-Dichloro-2-methoxybenzoic
acid (DICAMBA)
I

The nitrosylsulfuric acid used in the step-1 of diazotizing can be prepared by reacting nitric acid with $SO_2$.

In accordance with the embodiments of the present disclosure, the molar ratio of 2,5-dichloroaniline (II) and nitrosylsulfuric acid used for diazotizing can be in the range of 1:1 to 1:1.5.

In accordance with the preferred embodiment of the present disclosure, the molar ratio of 2,5-dichloroaniline (II) and nitrosylsulfuric acid used for diazotizing can be in the range of 1:1.03 to 1:1.2.

In accordance with one embodiment of the present disclosure, the molar ratio of 2,5-dichloroaniline (II) and nitrosylsulfuric acid used for diazotizing is 1:1.1.

Nitrosylsulfuric acid is in the form of an aqueous solution.

In accordance with the embodiments of the present disclosure, the concentration of nitrosylsulfuric acid in an aqueous solution can be in the range of 10% to 40% w/w.

In accordance with the preferred embodiment of the present disclosure, the concentration of nitrosylsulfuric acid in the aqueous solution is in the range of 25% to 40% w/w.

In accordance with the embodiments of the present disclosure, in the step of diazotizing, a solution of 2,5-dichloroaniline (II) in the first fluid medium is slowly added to nitrosylsulfuric acid over a period of time, in order to maintain the temperature of the reaction mass in the range of 15 to 30° C. The slow addition helps in controlling the temperature of the reaction mixture thereby increasing the yield of 2,5-dichlorophenyldiazonium salt by preventing its decomposition. In aqueous solution, 2,5-dichlorophenyldiazonium salts are unstable at temperatures above 50° C., as the diazonium group tends to decompose and liberate $N_2$ (nitrogen gas), thereby resulting in a reduced yield.

In accordance with the embodiments of the present disclosure, the addition of 2,5-dichloroaniline (II) to nitrosylsulfuric acid is carried out over a period of time in the range of 1 hour to 50 hours.

In accordance with one embodiment of the present disclosure, the slow addition of 2,5-dichloroaniline (II) to nitrosylsulfuric acid is carried out for 5 hours.

In accordance with one embodiment of the present disclosure, the first fluid medium is at least one selected from the group consisting of dichloromethane, 1,2-dichloroethane (EDC), chloroform, and carbon tetrachloride. Other fluid media can be used for diazotization.

In accordance with the embodiments of the present disclosure, the amount of the first fluid medium used for diazotization can be in the range of 100 ml/mole to 2000 ml/mole of 2,5-dichloroaniline (II).

In accordance with one embodiment of the present disclosure, the first fluid medium used for diazotizing 2,5-dichloroaniline (II) is 1,2-dichloroethane (EDC) and the amount of 1,2-dichloroethane (EDC) is 250 ml/mole of 2,5-dichloroaniline (II).

The diazotization is carried out under an inert atmosphere with stirring in a suitable reactor.

In accordance with the embodiments of the present disclosure, the diazotization is carried out at a temperature in the range of −15 to 50° C.

In accordance with the preferred embodiment of the present disclosure, the diazotization is carried out at a temperature in the range of 0 to 40° C.

In accordance with one embodiment of the present disclosure, the diazotization is carried out at a temperature of 15° C.

On completion of the diazotization, the unreacted nitrosylsulfuric acid present in the diazotizing reaction mixture is quenched by adding sulfamic acid or urea to form a diazonium salt thereof, which decomposes. After quenching of excess nitrosylsulfuric acid, the resultant diazotized reaction mixture is separated into an aqueous bottom phase and an organic top phase. The aqueous bottom phase containing 2,5-dichlorophenyldiazonium salt is taken directly to the step of hydroxylation.

In the hydroxylation step, the aqueous phase containing 2,5-dichlorophenyldiazonium salt obtained from the diazotizing step is slowly added over a period of time to sulfuric acid having a concentration in the range of 60% to 75% w/w. The rate of addition is controlled, in order to maintain the temperature of the hydroxylating reaction mixture in the range of 150 to 170° C. The reason for maintaining the temperature in this range is that, below 150° C., 2,5-dichloroaniline couples with 2,5-dichlorophenyldiazonium salt leading to the formation of by-products, while above 180° C., sulfuric acid degrades leading to $SO_2$ liberation, thereby causing safety hazards.

Steam is purged through the hydroxylating reaction mass and 2,5-dichlorophenol is isolated from the reaction mass by steam distillation.

In accordance with the embodiments of the present disclosure, the addition of 2,5-dichlorophenyldiazonium salt (III) to sulfuric acid is carried out over a period of time in the range of 1 hour to 20 hours.

In accordance with the preferred embodiment of the present disclosure, the addition of 2,5-dichlorophenyldiazonium salt (III) to sulfuric acid is carried out over a period of time in the range of 2 hour to 12 hours.

In accordance with one embodiment of the present disclosure, the addition of 2,5-dichlorophenyldiazonium salt (III) to sulfuric acid is carried out for 8 hours.

In accordance with the embodiments of the present disclosure, in the step of hydroxylating, the yield of 2,5-dichlorophenol (IV) is 95 to 98 mole %.

In accordance with the embodiments of the present disclosure, recovery of sulfuric acid from the residue comprising sulfuric acid, obtained in the hydroxylating step, involves the following steps.

The residue comprising sulfuric acid is contacted with 1,2-dichloroethane (50 to 100 ml/mole) at a temperature in the range of 70 to 100° C. to obtain a biphasic mixture comprising an organic phase and an aqueous phase containing sulfuric acid.

The aqueous phase is separated from the biphasic mixture. The separated aqueous phase containing sulfuric acid, having concentration in the range of 60 to 65% w/w, is concentrated by distilling out water to obtain sulfuric acid having a concentration in the range of 78 to 82% w/w. The organic phase (EDC), obtained as a result of separation of the aqueous phase containing sulfuric acid from the biphasic mixture, is distilled to recover EDC.

The resulting sulfuric acid is further contacted with 0.2% to 0.6% w/w concentrated nitric acid, at a temperature in the range of 80 to 130° C., to obtain recovered sulfuric acid.

In accordance with the embodiments of the present disclosure, the alkali metal hydroxide used for forming alkali metal 2,5-dichlorophenolate (V) is at least one selected from the group consisting of sodium hydroxide, potassium hydroxide, and lithium hydroxide.

The formation of alkali metal 2,5-dichlorophenolate (V) is carried out using an alkali metal hydroxide (M-OH) in a second fluid medium.

In accordance with the embodiments of the present disclosure, the molar ratio of 2,5-dichlorophenol (IV) and the amount of the alkali metal hydroxide used for forming the alkali metal 2,5-dichlorophenolate is in the range of 1:0.9 to 1:1.1.

In accordance with one embodiment of the present disclosure, the alkali metal hydroxide used for forming the alkali metal 2,5-dichlorophenolate (V) is potassium hydroxide, and the molar ratio of 2,5-dichlorophenol (IV) and potassium hydroxide is 1:0.98. The potassium hydroxide is in the form of flakes or lye having strength in the range from 48% to 50% w/w.

In accordance with the embodiments of the present disclosure, the second fluid medium may be selected from the group consisting of benzene, toluene, and xylene. Other fluid media can be used for forming alkali metal 2,5-dichlorophenolate (V).

The step of forming alkali metal 2,5-dichlorophenolate (V) is carried out under an inert atmosphere in a suitable reactor under stirring.

In accordance with the embodiments of the present disclosure, the step of forming the alkali metal 2,5-dichlorophenolate (V) is carried out at a temperature in the range of 50 to 150° C.

In accordance with the preferred embodiment of the present disclosure, the step of forming the alkali metal 2,5-dichlorophenolate (V) is carried out at a temperature in the range of 80 to 120° C.

In accordance with one embodiment of the present disclosure, the step of forming the alkali metal 2,5-dichlorophenolate (V) is carried out at 110° C.

The moisture content of the solution containing the alkali metal 2,5-dichlorophenolate (V) is reduced by azeotropic removal of water. In accordance with one embodiment of the present disclosure, the moisture content of the alkali metal 2,5-dichlorophenolate (V) is below <0.1%.

In accordance with the embodiments of the present disclosure, the period of time for forming the alkali metal 2,5-dichlorophenolate (V) is in the range of 1 hour to 15 hours.

In accordance with one embodiment of the present disclosure, the period of time for forming the alkali metal 2,5-dichlorophenolate (V) is 5 hours.

In accordance with one embodiment of the present disclosure, the yield of potassium 2,5-dichlorophenolate (V) is in the range of 96 to 98 mole %.

The potassium 2,5-dichlorophenolate (V) is dissolved in xylene to form a clear solution and is carboxylated with carbon dioxide ($CO_2$).

In accordance with the embodiments of the present disclosure, the step of carboxylating is carried out with $CO_2$ at a pressure in the range of 5 kg/cm² to 50 kg/cm².

In accordance with the preferred embodiment of the present disclosure, the step of carboxylating is carried out with $CO_2$ at a pressure in the range of 10 kg/cm² to 40 kg/cm².

In accordance with one embodiment of the present disclosure, the step of carboxylating is carried out with $CO_2$ at a pressure of 30.0 kg/cm².

In accordance with the embodiments of the present disclosure, the carboxylation is carried out at a temperature in the range of 60 to 160° C.

In accordance with one embodiment of the present disclosure, the carboxylation is carried out at a temperature of 130° C.

In accordance with the embodiments of the present disclosure, the carboxylation is carried out over a period of time in the range of 2 hours to 20 hours.

In accordance with the preferred embodiment of the present disclosure, the carboxylation is carried out over a period of time in the range of 4 hours to 10 hours.

In accordance with one embodiment of the present disclosure, the carboxylation is carried out for 7 hours.

The carboxylated mass is filtered at a temperature in the range of 110 to 120° C. to isolate the dipotassium salt of 3,6-dichlorosalicylic acid (VI).

The yield of the dipotassium salt of 3,6-dichlorosalicylic acid (VI) is in the range of 30 to 35 mole %.

The dipotassium salt of 3,6-dichlorosalicylic acid (VI) is methylated using a methylating agent such as methyl chloride ($CH_3Cl$) and dimethyl sulfate ($(CH_3)_2SO_4$) in at least one third fluid medium.

The third fluid medium can be selected from the group consisting of methanol, ethanol, isopropanol, and butanol. Other fluid media can be used for methylation.

In accordance with one embodiment of the present disclosure, the third fluid medium is methanol.

In accordance with the embodiments of the present disclosure, the dipotassium salt of 3,6-dichlorosalicylic acid (VI) can be methylated under $CH_3Cl$ pressure in the range of 2 kg/cm² to 15 kg/cm².

In accordance with the preferred embodiments of the present disclosure, the dipotassium salt of 3,6-dichlorosalicylic acid (VI) is methylated under $CH_3Cl$ pressure in the range of 6 kg/cm² to 12 kg/cm².

In accordance with one embodiment of the present disclosure, the dipotassium salt of 3,6-dichlorosalicylic acid (VI) is methylated under $CH_3Cl$ pressure of 6 kg/cm².

In accordance with one embodiment of the present disclosure, the dipotassium salt of 3,6-dichlorosalicylic acid (VI) is methylated at a temperature of 60 to 160° C.

In accordance with one embodiment of the present disclosure, the dipotassium salt of 3,6-dichlorosalicylic acid (VI) is methylated for a period of 8 hours.

The methylated mass is filtered at a temperature in the range of 50 to 55° C. to remove potassium chloride (KCl). The filtrate of the methylated mass comprises methyl 3,6-dichloro-2-methoxy benzoate (DICAMBA ester, VII), 3,6-dichloro-2-methoxybenzoic acid (DICAMBA, I), dipotassium salt of 3,6-dichlorosalicylic acid (VI), and 2,4-dichloroanisole. The third fluid medium is distilled off from the filtrate to obtain a resultant mass.

Xylene and water are added to the resultant mass to obtain a biphasic mixture. The pH of the biphasic mixture is adjusted in the range of 11 to 12 by carefully adding an inorganic base such as NaOH, KOH or $Na_2CO_3$. Organic phase and aqueous phase of the biphasic mixture are separated. The organic phase is distilled to provide a mixture of DICAMBA ester (VII), and dichloroanisole. The distilled fraction has a composition of 90% DICAMBA ester (VII), and 10% dichloroanisole GLC area %.

Further, xylene is distilled out as a first fraction during this distillation. The distilled xylene is recovered and recycled in the step of forming the alkali metal 2,5-dichlorophenolate.

The aqueous phase separated from the biphasic mixture contains alkali metal salts of DICAMBA (I), and 3,6-dichlorosalicylic acid (VI), which can be recycled in methylation step.

The yield of DICAMBA ester (VII) is in the range of 95 to 98 mole %.

DICAMBA ester (VII) is hydrolyzed with an alkali selected from the group consisting of sodium hydroxide, potassium hydroxide, and lithium hydroxide.

In accordance with the embodiments of the present disclosure, the molar ratio of DICAMBA ester (VII) and the alkali used for hydrolysis can be in the range of 2:1 to 1:2.

In accordance with one embodiment of the present disclosure, the alkali is NaOH and the molar ratio of DICAMBA ester (VII) and NaOH used for hydrolysis is 1:1.

Mixture of DICAMBA ester (VII) and dichloroanisole obtained from the methylating step is subjected to selective hydrolysis with an alkali at a temperature in the range of 50 to 130° C.

DICAMBA ester contains two hydrolysable groups i.e., an ester group and an ether group. Further, 2,5-dichloroanisole contains a hydrolysable ether group. By using one mole of alkali per mole of DICAMBA ester (VII), the ester group is selectively hydrolysed over the ether group with the alkali at a temperature in the range of 50 to 130° C. thereby, providing DICAMBA with higher purity.

In accordance with the embodiments of the present disclosure, in the step of hydrolyzing, the yield of DICAMBA (I) is in the range of 97 to 98% with purity in the range of 97.5 to 98.5 mole %.

In accordance with the embodiments of the present disclosure, the process of the present disclosure further includes an additional step of dissolving the DICAMBA obtained in the step of hydrolysing, in a fourth fluid medium, to obtain a solution and recrystallizing DICAMBA from the solution. The recrystallized DICAMBA has a purity of 99% or greater.

In accordance with embodiments of the present disclosure, the fourth fluid medium is at least one selected from the group consisting of water and xylene.

In accordance with one embodiment of the present disclosure, the DICAMBA obtained from the hydrolysing step is recrystallized from a mixture of water (300 ml/mole) and xylene (50 ml/mole). The DICAMBA crystals are washed with xylene (50 ml/mole).

In accordance with embodiments of the present disclosure, the purity of the recrystallized DICAMBA is in the range of 99.0 to 99.9%.

The process of the present disclosure uses commonly available and inexpensive reagents and fluid media and recycles the fluid media as well as some of the by-products. Hence, the process of the present disclosure is simple and economical.

The disclosure will now be described with reference to the accompanying example which does not limit the scope and ambit of the disclosure. The description provided is purely by way of example and illustration.

The laboratory scale example provided herein can be scaled up to industrial or commercial scale.

EXAMPLE

Step 1: Diazotization of 2,5-dichloroaniline (II) with Nitrosylsulfuric Acid

Nitrosylsulfuric acid (1.05 equivalents) was received in a stainless steel (SS) reactor and the reactor was cooled to 15° C. A solution of 2,5 dichloroaniline (162 g, 1 mole) in 1,2-dichloroethane (250 ml) was fed to the reactor over 4 hours, while maintaining the reactor temperature below 20° C. by controlling the flow rate of addition of 2,5-dichloroaniline (DCA) solution while agitating the solution at a speed of ~400 rpm with a 80% twisted turbine stirrer. On completion of addition of 2,5-dichloroaniline (DCA) solution, the reaction mixture was further agitated for an hour. Completion of reaction was indicated by complete consumption of 2,5-dichloroaniline. The reaction mixture was quenched by addition of sulfamic acid ($HSO_3NH_2$), in order to form a diazonium salt of sulfamic acid with excess of nitrosylsulfuric acid. The diazonium salt of sulfamic acid decomposed. The reaction mass was allowed to stand, wherein it separated into two phases; an aqueous phase containing 2,5-dichlorophenyldiazonium salt and an organic 1,2-dichloroethane phase. The aqueous phase containing 2,5-dichlorophenyldiazonium salt was taken as such to the next step of hydroxylation.

Yield of 2,5-dichlorophenyldiazonium salt was found to be 98 mole %

Step 2: Hydroxylation of 2,5-dichlorophenyldiazonium salt (III) with Sulfuric Acid ($H_2SO_4$)

The aqueous phase containing the 2,5-dichlorophenyldiazonium salt obtained in step-1, was fed over 8 hours into a glass lined reactor containing 70% (wt/wt) sulfuric acid solution at 160° C. to obtain a reaction mass. Steam was continuously purged into reaction mass while maintaining the temperature at 160° C. to obtain 2,5-dichlorophenol by steam distillation. During this operation, 2,5-dichlorophenol was azeotropically collected from the reaction mass. The distillate was collected in a heated vessel (85° C.), where the condensed distillate forms two phases with a bottom phase of molten 2,5-dichlorophenol and an aqueous phase. The bottom phase of 2,5-dichlorophenol was separated and the aqueous phase was extracted with xylene, and mixed with 2,5-dichlorophenol. The xylene and the 2,5-dichlorophenol organic phase were washed with water to remove mineral acidity to obtain 2,5-dichlorophenol with a yield of 98 mole %.

The step of hydroxylating 2,5-dichlorophenyldiazonium salt also yielded a residue comprising sulfuric acid. The residue comprising sulfuric acid was extracted with 1,2-dichloroethane (50 to 100 ml/mole), at a temperature of 85° C. to obtain a biphasic mixture comprising an organic phase (EDC) and an aqueous phase containing sulfuric acid. The aqueous phase containing sulfuric acid was separated from the biphasic mixture. The separated aqueous phase containing sulfuric acid, having concentration of 63% w/w, was concentrated by distillation of water to obtain sulfuric acid with concentration of 80% w/w. The resulting sulfuric acid was further treated with 0.5% w/w concentrated nitric acid at a temperature of 110° C. to obtain recovered sulfuric acid.

The organic phase (EDC), obtained as a result of separation of the aqueous phase containing sulfuric acid from the biphasic mixture, is distilled to recover EDC.

Step 3: Forming Potassium Salt of 2,5-dichlorophenolate 2,5-dichlorophenol (163 g, 1 mole) obtained in step-2, was dissolved in xylene (700 ml) in an SS reactor agitated with 80% twisted turbine stirrer at 250 rpm. Aqueous potassium hydroxide solution (0.99 equivalents) was added to the above 2,5-dichlorophenol solution over 1 hour with continuous stirring to obtain a reaction mixture. On completion of the reaction, the reaction mixture was subjected to azeotropic distillation for removal of water by heating at 110° C. to obtain potassium salt of 2,5-dichlorophenolate in xylene. The moisture content of the resultant dehydrated solution of potassium 2,5-dichlorophenolate in xylene was <0.01%. Potassium 2,5-dichlorophenolate content of xylene was 1.9 N. The solution of potassium 2,5-dichlorophenolate in xylene was used as such for the next step of carboxylation.

Step 4: Carboxylation of Potassium 2,5-dichlorophenolate with Carbon Dioxide ($CO_2$)

The clear solution of potassium 2,5-dichlorophenolate in xylene obtained in step-3, was transferred to a high pressure stainless steel (SS) reactor and the content was heated to 130° C. The $CO_2$ pressure in the reactor was maintained at 30 kg/cm$^2$ for 7 hours until no more $CO_2$ was consumed by the reaction mixture. The reaction mixture was cooled to 110° C. by jacketed cooling, excess of $CO_2$ was vented out, recovered back and recycled. Under these conditions the reaction mixture formed a slurry which was filtered at 110° C. and washed (×2) with hot xylene at 100° C. to obtain dipotassium salt of 3,6-dichlorosalicylic acid (VI) with 33 mole % yield.

Step 5: Methylation of Dipotassium Salt of 3,6-dichlorosalicylic Acid with Methyl Chloride ($CH_3Cl$)

In a high pressure stainless steel (SS) reactor, dipotassium 3,6-dichlorosalicylic acid obtained in step-4, was re-slurred in methanol (400 ml/mole) at 90° C. and methyl chloride was introduced into the reactor to attain a pressure of 6 kg/cm$^2$. The reaction was monitored for unreacted dipotassium 3,6-dichlorosalicylic acid. After completion of the reaction, the reaction mass was filtered to collect KCl cake. The filtrate contained methyl, 3,6-dicloro-2-methoxybenzoate (DICAMBA ester), 3,6-dichlorosalicylic acid (DCSA), 3,6-dichloro-2-methoxy benzoic acid (DICAMBA) and 2,5-dichloroanisole (DCA). Methanol was recovered for reuse. Water and xylene were added to the residual mass and aqueous KOH solution was added to the reaction mass until the pH of the reaction mass was 12. At the pH of 12, dipotassium 3,6-dichlorosalicylic acid and 3,6-dichloro-2-methoxy benzoic acid (DICAMBA) dissolved in the aqueous phase as their salts while DICAMBA ester and dicholoroanisole remained in the organic xylene layer. The organic layer was subjected to fractional distillation at 135° C. under reduced pressure. Xylene was collected as first fraction followed by dicholoroanisole, and DICAMBA ester in that order. The distilled fraction of DICAMBA ester was composed of 90% DICAMBA ester, and 10% dichloroanisole. The overall yield of DICAMBA ester was 97 mole %.

Step 6: Hydrolysing DICAMBA Ester with an Alkali

3,6-Dichloro-2-methoxybenzoic acid (DICAMBA)

The distilled fraction obtained in step-5, comprising DICAMBA ester and 2,5-dichloroanisole, was mixed with aqueous NaOH (4.0 N, 1.0 equi/mole) and the resultant mixture was heated at 105° C. After completion of hydrolysis, the reaction mixture was cooled to 80° C. The reaction mixture at 80° C. was mixed with xylene and stirred at 80° C. Stirring was stopped and the reaction mixture was allowed to settle to obtain a biphasic mixture containing an organic phase and an aqueous phase. The aqueous phase was separated and acidified at 80° C. to pH=1 with HCl. Upon adjusting pH, the resultant mixture formed a biphasic mixture comprising an aqueous phase and an organic phase. The organic phase at the bottom, containing molten DICAMBA, was separated at 80° C., washed with water to free it from mineral acidity and dried under reduced pressure at 110° C. to remove trapped moisture. The DICAMBA was obtained with yield of 97 mole % and a purity of 98.0%.

Water (300 ml/mole) and xylene (50 ml/mole) were added to the DICAMBA and the resultant mixture was heated under reflux. The reaction mixture was cooled to 15° C. The precipitate formed was filtered and washed with 50 ml/mole xylene to obtain DICAMBA crystals with purity of 99.6%.

Methanol formed during hydrolysis was recycled for reuse.

Technical Advances and Economical Significance

The process of the present disclosure described herein above has several technical advantages including, but not limited to, the realization of a process for preparing 3,6-Dichloro-2-methoxybenzoic acid (DICAMBA), that is simple; and provides high yield and high purity.

The embodiments herein and the various features and advantageous details thereof have been explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for preparing 3,6-dichloro-2-methoxybenzoic acid (DICAMBA), said process comprising:
    (a) diazotizing 2,5-dichloroaniline with nitrosylsulfuric acid in at least one first fluid medium at a temperature in the range of 15° C. to 50° C. to obtain 2,5-dichlorophenyldiazonium salt;
        wherein the first fluid medium is selected from the group consisting of dichloromethane, 1,2-dichloroethane (EDC), chloroform, and carbon tetrachloride;
    (b) hydroxylating the 2,5-dichlorophenyldiazonium salt by contacting the 2,5-dichlorophenyldiazonium salt with sulfuric acid at a temperature in the range of 150° C. to 170° C. to obtain 2,5-dichlorophenol and a residue comprising sulfuric acid, wherein the concentration of the sulfuric acid used for hydroxylating is in the range of 60% to 75% w/w, and wherein the residue comprising sulfuric acid is subjected to recovery of sulfuric acid, and wherein yield of 2,5-dichlorophenol is in the range of 95 mole % to 98 mole %;
    (c) forming alkali metal 2,5-dichlorophenolate by reacting 2,5-dichlorophenol with an alkali metal hydroxide in at least one second fluid medium, wherein the moisture content of the alkali metal 2,5-dichlorophenolate is in the range of 0.005 to 0.05% w/w;
    (d) carboxylating the alkali metal 2,5-dichlorophenolate at a temperature in the range of 60° C. to 160° C. to obtain alkali metal salt of 3,6-dichlorosalicylic acid;
    (e) methylating the alkali metal salt of 3,6-dichlorosalicylic acid, in at least one third fluid medium, with a methylating agent selected from the group consisting of methyl chloride (CH3Cl) and dimethyl sulfate ((CH$_3$)$_2$SO$_4$) at a temperature in the range of 60° C. to 160° C. to obtain methyl 3,6-dichloro-2-methoxybenzoate (DICAMBA ester); and
    (f) hydrolysing the DICAMBA ester at a temperature in the range of 50° C. to 130° C. to obtain DICAMBA;
    wherein the step of diazotizing involves slow addition of a solution of 2,5-dichloroaniline in the first fluid medium to nitrosylsulfuric acid, wherein the slow addition is carried out over a time period in the range of 4-50 hours by controlling a temperature of the reaction, thereby preventing decomposition of diazonium salt; and
    wherein said DICAMBA has a yield in the range of 97% to 98% and purity in the range of 97.5% to 99.6%.

2. The process as claimed in claim 1, wherein the molar ratio of the amount of 2,5-dichloroaniline to the amount of nitrosylsulfuric acid is in the range of 1:1 to 1:1.5.

3. The process as claimed in claim 1, wherein the nitrosylsulfuric acid is in the form of an aqueous solution having a concentration in the range of 10% to 40% w/w.

4. The process as claimed in claim 1, wherein the step of diazotizing involves quenching unreacted nitrosylsulfuric acid by sulfamic acid or urea.

5. The process as claimed in claim 1, wherein the step of hydroxylating involves purging steam through the reaction mass to obtain 2,5-dichlorophenol by steam distillation.

6. The process as claimed in claim 1, wherein the step of hydroxylating is carried out for a time period in the range of 2 to 20 hours.

7. The process as claimed in claim 1, wherein the recovery of sulfuric acid from the residue comprising sulfuric acid obtained in the hydroxylating step involves the following steps:
    I. contacting the residue comprising sulfuric acid with 1,2-dichloroethane (EDC) at a temperature in the range of 70° C. to 100° C. to obtain a biphasic mixture comprising an organic phase and an aqueous phase containing sulfuric acid;
    II. separating the aqueous phase from the biphasic mixture, concentrating the separated aqueous phase to obtain sulfuric acid having a concentration in the range of 78 to 82% w/w, wherein EDC is recovered from the separated organic phase; and
    III. contacting sulfuric acid obtained in step-II with 0.2 to 0.6% w/w concentrated nitric acid at a temperature in the range of 80° C. to 130° C. to obtain recovered sulfuric acid.

8. The process as claimed in claim 1, wherein the alkali metal hydroxide used for forming the alkali metal 2,5-dichlorophenolate is at least one selected from the group consisting of sodium hydroxide, potassium hydroxide, and lithium hydroxide.

9. The process as claimed in claim 1, wherein the alkali metal hydroxide used for forming the alkali metal 2,5-dichlorophenolate is potassium hydroxide.

10. The process as claimed in claim 1, wherein the alkali metal hydroxide used for forming the alkali metal 2,5-dichlorophenolate is 50.0% w/w potassium hydroxide lye or potassium hydroxide flakes.

11. The process as claimed in claim 1, wherein the molar ratio of the amount of 2,5-dichlorophenol and the amount of the alkali metal hydroxide is in the range of 1:0.98 to 1:1.1.

12. The process as claimed in claim 1, wherein the second fluid medium is selected from the group consisting of benzene, toluene, and xylene.

13. The process as claimed in claim 1, wherein the second fluid medium is xylene.

14. The process as claimed in claim 1, wherein the step of carboxylation (step d) is carried out with carbon dioxide ($CO_2$) at a pressure in the range of 5 kg/cm$^2$ to 50 kg/cm$^2$.

15. The process as claimed in claim 1, wherein the step of carboxylation (step d) is carried out with $CO_2$ at a pressure in the range of 25 kg/cm$^2$ to 35 kg/cm$^2$.

16. The process as claimed in claim 1, wherein the third fluid medium is at least one selected from the group consisting of methanol, ethanol, propanol, and butanol.

17. The process as claimed in claim 1, wherein the third fluid medium is methanol.

18. The process as claimed in claim 1, wherein the step of methylation step e) is carried out with methyl chloride ($CH_3Cl$) at a pressure in the range of 5 kg/cm$^2$ to 15 kg/cm$^2$.

19. The process as claimed in claim 1, wherein the hydrolysis (step f) of DICAMBA ester is carried out with an aqueous alkali solution; or wherein the molar ratio of the amount of the alkali to the amount of DICAMBA ester is in the range of 1:1 to 1:2.

20. The process as claimed in claim 1, which includes an additional step of dissolving the DICAMBA obtained in step (f) in a fourth fluid medium to obtain a solution and recrystallizing DICAMBA from said solution, wherein said recrystallized DICAMBA has a purity of 99.0% or greater; or wherein the fourth fluid medium is at least one selected from the group consisting of water and xylene.

\* \* \* \* \*